US005476660A

United States Patent [19]

Somasundaran et al.

[11] Patent Number: 5,476,660

[45] Date of Patent: Dec. 19, 1995

[54] DEPOSITION OF MATERIALS TO SURFACES USING ZWITTERIONIC CARRIER PARTICLES

[75] Inventors: Ponisseril Somasundaran, Nyack; Kavssery P. Ananthapadmanabhan, New Windsor, both of N.Y.; Mitsuko Fujiwara, Edgewater; Liang S. Tsaur, Norwood, both of N.J.

[73] Assignee: Lever Brothers Company, Division of Conopco, Inc., New York, N.Y.

[21] Appl. No.: 285,270

[22] Filed: Aug. 3, 1994

[51] Int. Cl.[6] .................... A61K 7/00; A61K 9/14

[52] U.S. Cl. .................... 424/401; 424/489; 424/61; 424/69; 424/70.11

[58] Field of Search .................... 424/401, 489, 424/502, 61, 69, 70.11, 70.17

[56] References Cited

U.S. PATENT DOCUMENTS

| | | | |
|---|---|---|---|
| 3,761,418 | 9/1973 | Parran, Jr. | 252/106 |
| 4,659,564 | 4/1987 | Cox et al. | 424/65 |
| 4,673,525 | 6/1987 | Small et al. | 252/132 |
| 4,753,793 | 6/1988 | Walton | 424/70.27 |
| 4,798,721 | 1/1989 | Yahagi | 428/402 |
| 4,820,447 | 4/1989 | Medcalf, Jr. et al. | 252/117 |
| 4,871,536 | 10/1989 | Arraudeau et al. | 424/59 |
| 5,064,555 | 11/1991 | Medcalf, Jr. et al. | 252/11 |
| 5,171,264 | 12/1992 | Merrill | 623/3 |
| 5,215,757 | 6/1993 | El-Nokaly | 424/490 |
| 5,219,561 | 6/1993 | Gagnebien | 424/69 |
| 5,372,804 | 12/1994 | Khoshdel et al. | 424/59 |

FOREIGN PATENT DOCUMENTS

| | | |
|---|---|---|
| 1439244 | 6/1976 | European Pat. Off. . |
| 0093601 | 11/1983 | European Pat. Off. . |
| 0573229 | 8/1993 | European Pat. Off. . |

OTHER PUBLICATIONS

Co-pending application Ser. No. 08/071,278.

"Nonaqueous Silica Dispersions Stabilized by Terminally-Grafted Polystyrene Chains", *Journal of Colloid and Interface Science,* vol. 68, No. 1, Jan. 1979, pp. 190–195.

Onoda et al., "Two-and One-Dimensional Flocculation of Silica Spheres on Substrates", *Journal of Colloid and Interface Science,* vol. 8, No. 1, Jul. 1987, pp. 169–175.

Kitchener, J. A., "Surface Forces in the Deposition of Small Particles", *Journal Soc. Cosmet. Chem.,* vol. 24, (1973), pp. 709–725.

*Primary Examiner*—Thurman K. Page
*Assistant Examiner*—Sally Gardner
*Attorney, Agent, or Firm*—Rimma Mitelman

[57] ABSTRACT

Compositions to deposit an active substance on a target surface (i.e. fabric, sun, hair, teeth). The active substance is left on the surface, after the product is rinsed off the surface. The preferred deposition is from compositions containing an anionic or nonionic active in the co-presence of an anionic surfactant. The compositions contain carrier particles having a zwitterionic or cationic surface and a plurality of outwardly protruding filaments containing charged organocarbyl groups. The active substance is contained within the carrier particles.

16 Claims, No Drawings

DEPOSITION OF MATERIALS TO SURFACES USING ZWITTERIONIC CARRIER PARTICLES

FIELD OF THE INVENTION

The invention relates to compositions for depositing an active substance onto a target surface, methods of preparing the compositions, and methods of using the compositions.

BACKGROUND OF THE INVENTION

Many household products and personal products contain active ingredients which need to be delivered to and deposited on a target surface, i.e., fabric, skin, hair, or teeth. The product must leave the active ingredient (e.g., a perfume or an antimicrobial agent) on the target surface after the product is washed and rinsed off the surface. Since these surfaces are negatively charged, the usual approach for deposition from "leave off" products is to use cationic actives for deposition. Deposition of anionic actives from aqueous solutions onto anionic surfaces can be also achieved by using cationic polymers as deposition aids. For example, cationic polymers can be used to promote the adsorption of artionic surfactants such as sodium dodecyl sulfate onto anionic silica particles. Similarly, cationic polymers may also be used to deposit silica particles onto glass.

Deposition of anionic or nonionic actives onto anionic surfaces from compositions containing anionic surfactants is much more difficult. Unfortunately, a great number of household and personal products (e.g., shampoos, toothpaste, soap bar, and skin cleansing compositions) contain anionic surfactants. Anionic surfactants interfere with deposition by adsorbing on all surfaces as well as forming complexes/precipitates with cationic deposition aids. Even if the deposition occurs, the formulations may exhibit poor stability due to flocculation and precipitation, particularly at high concentration of an anionic active and/or at a high concentration of an anionic surfactant. Silicone oil droplets dispersed in shampoo can be deposited onto hair using a commercially available cationic polymer, Jagua® available from Rhone-Poulenc. See e.g., European Patent Application 093 601. However, the higher the concentration of an anionic surfactant, the harder it is to attain deposition of actives. Thus, it is desirable to improve the deposition of actives onto a negatively charged target surface in the presence of an artionic surfactant.

There is a need for compositions and methods for effective delivery and deposition of active substances onto negatively charged surfaces, particularly when compositions also contain anionic surfactants.

The use of nonionic "hairy" structures for steric stabilization of particles in different media has been described in "Nonaqueous Silica Dispersions Stabilized by Terminally-Grafted Polystyrene Chains", Journal of Colloid and Interface Science, Vol. 68, No. 1, (January 1979), pp. 190–195. This document, however, does not address the problem of deposition at all. There have been attempts also to use functionalized materials for deposition onto surfaces. (See e.g., U.S. Pat. No. 5, 171,264). These documents, however, do not address the problem of deposition in the presence of anionic surfactants.

Accordingly, it is an object of the present invention to provide a composition for delivery and deposition of an active substance to a target surface while avoiding the disadvantages of the prior art.

It is another object of the present invention to provide compositions for depositing active substances with a negative charge (acquired or inherent) from compositions containing an anionic surfactant, even at high concentrations, onto a negatively charged surface.

It is another object of the invention to provide compositions and methods for depositing active substances onto a target surface, so that the active stays on the surface after the compositions containing the active have been rinsed off.

It is still another object of the invention to provide methods of making and using the compositions for depositing active substances onto a target surface.

These and other objects of the invention will become more apparent from the detailed description and examples that follow.

SUMMARY OF THE INVENTION

The above objects are attained by the present invention which includes, in part, a composition for depositing an active substance onto a target surface, the composition containing (i) from about 0.1% to about 50% of carrier particles selected from the group consisting of:

(a) particles with a zwitterionic surface, the surface having a plurality of outwardly protruding filaments containing positively charged organocarbyl groups and a plurality of outwardly protruding filaments containing negatively charged organocarbyl groups; and (b) particles with a cationic surface, the surface having a plurality of outwardly protruding filaments containing positively charged organocarbyl groups;

(ii) from about 0.01% to about 50% of an active substance within said particle.

In a preferred embodiment of the invention, the composition further includes a cationic or an amphoteric polymer deposition aid, The term "zwitterionic" as employed herein means a mixture of cationic and anionic (not necessarily neutral); thus the surface of the zwitterionic particle must have both cationic and anionic groups (i.e., positively charged and negatively charged organocarbyl groups).

The term "a plurality of outwardly protruding filaments" as used herein means that a plurality of chemical chains protrude outwardly from the surface of the particles, in essence forming a filamentous, hairy-like surface. The term "organocarbyl groups" means chemical groups or moieties comprised of at least carbon and hydrogen, and optionally of heteroatoms, such as oxygen, nitrogen, phosphorus, and sulphur. Suitable examples of negatively charged organocarbyl groups include, but are not limited to sulfate, sulfonate, carboxylate, phosphate groups, and mixtures thereof. Suitable examples of positively charged organocarbyl groups include but are not limited to primary amine, secondary amine, tertiary amine, quaternary ammonium salts, amidines, pyridinium salts and mixtures thereof.

The term "particles" includes solid and semi-solid particles, as well as emulsion droplets.

The zwitterionic or cationic particles employed in the present invention serve as carrier particles for an active material which is entrapped in or distributed throughout the carrier particles. In use, when the inventive compositions are applied to a target surface, the active material is delivered to and deposited onto a target surface by virtue of the deposition of the carrier particles.

The present invention is based at least in part on the discovery that particles having a filamentous zwitterionic or cationic surface deposit onto negatively charged surfaces to a substantially greater extent than the particles with filamentous anionic surface. Unlike the anionic particles, the zwitterionic or cationic particles remain on the target surface even after the target surface is washed off. In a preferred embodiment of the invention, zwitterionic rather than cationic particles are employed in order to minimize or eliminate the formation of flocs upon standing in an anionic surfactant system. The deposition of the particles employed in the present invention is substantially enhanced by the co-presence of a deposition aid, which is selected from cationic or amphoteric polymers.

The inventive compositions are especially useful when it is desired to deposit an anionic active substance onto a negatively charged target surface from a composition which also contains an artionic surfactant, particularly when the concentration of an anionic surfactant is high, albeit the compositions may be employed for depositing any active substances present in any household or personal product composition. Thus, the compositions are most useful when it is desired to deposit an active substance, particularly an anionic active substance, from a laundry detergent, a dishwashing composition, a soap bar, a liquid skin cleansing composition, a shampoo, a toothpaste or a mouthwash.

The present invention also includes methods of preparing and using the inventive compositions.

DETAILED DESCRIPTION OF THE INVENTION

The inventive compositions contain, as a first essential ingredient, a particle which serves as a carrier for an active material. Suitable carrier particles must be insoluble in a final formulation in order to preserve the structural integrity of the particles during storage. Since consumer products are, for the most part, aqueous based, the carrier particles included in the inventive compositions are water-insoluble. However, the carrier particles must be water-dispersible so that uniform stable suspensions or emulsions can be formed. The carrier particles employed in the present invention have either a filamentous zwitterionic surface or a filamentous cationic surface. When zwitterionic carrier particles are employed in the invention, some filaments on the surface of the particles carry positively charged organocarbyl groups or moieties and others carry negatively charged organocarbyl groups or moieties. When cationic carrier particles are employed in the present invention, all filaments on the surface of the particles carry positively charged organocarbyl groups. Carrier particles having a filamentous zwitterionic or cationic surface deposit onto negatively charged surfaces to a substantially greater extent than the particles with filamentous anionic surfaces. Unlike the anionic particles, the zwitterionic or cationic particles remain on the target surface even after the target surface has been washed off. Although the zwitterionic particles used in the present invention may and preferably do have a net negative charge under neutral pH (i.e., "a net zeta potential"), they still deposit substantially better than anionic particles with the same net negative charge. Several factors may contribute to the higher deposition of zwitterionic particles over homoionic particle having the same net zeta potential. Although not wishing to be bound by this theory, inventors believe that changes in dynamic local potentials because of configurational changes of the filamentous structure as the zwitterionic surface approaches an anionic substrate surface may be playing a key role during deposition.

The filamentous zwitterionic or cationic surface of the carrier particles employed herein may be formed in several ways. For example, a water-insoluble material may be coated (e.g., coating by adsorption) with a polymer which has pendant negatively and positively charged side chains, the polymer thus forming a filamentous zwitterionic surface. When this approach is taken, suitable solid materials include but are not limited to porous silica, zeolite, latex particles. Suitable polymers are polyampholytes which have a neutral backbone and pendant anionic and pendant cationic group, e.g., acrylate/betaine copolymers, as described in U.S. Pat. No. 4,985,487, incorporated by reference herein; crosslinked anionic polymer/betaine polymer, as described in U.S. Pat. No. 5,098,699, incorporated by reference herein; zwitterionic gafquat-like materials, as described in U.S. Pat. No. 5,045,617, incorporated by reference herein; cationic/anionic/amphoteric combinations as described in U.S. Pat. No. 4,591,610, incorporated by reference herein; carboxylate/ammonium zwitterionic polymers as described in U.S. Pat. No. 3,836,537, incorporated by reference herein; detergent/zwitterionic polymer mixture as described in U.S. Pat. No. 4,075,131, incorporated by reference herein; crosslinked amphoteric polymer as described in U.S. Pat. No. 4,534,892, incorporated by reference herein; DMDAAC/acrylic acid copolymers as described in EP 269 243 and in EP 266 1111. When cationic carrier particles are desired, suitable polymers include but are not limited to the polymers described in U.S. Pat. Nos. 3,761,418; 4,673,525; 4,820,447; 5,064,555; and 4,871,536, all of which are incorporated by reference herein.

The preferred polymers are Polyquaternium (CTFA name) polymers, e.g., Polyquaternium-1, Polyquaternium-2, Polyquaternium-4, Polyquaternium-5, Polyquaternium-6, (also known as Merquat 100® available from Calgon), Polyquaternium-7 (also known as Merquat 550® available from Calgon), Polyquaternium-8, Polyquaternium-9, Polyquaternium-10 (also known as Polymer JR 400®), Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-24, Polyquaternium-27, Polyquaternium-28, Polyquaternium-29 (also known as Kytamer KC® available from Amerchol), Polyquaternium-30, Polyquaternium-31, Polyquaternium-32, Polyquaternium33, Polyquaternium-34, Polyquaternium-35, Polyquaternium-36, Polyquaternium-37, Polyquaternium-39.

Another way to obtain a carrier particle with a filamentous surface suitable for use in the present invention is to form an emulsion of molten wax at a temperature higher than room temperature and to obtain emulsion droplets of net positive or negative charge by adding a combination of anionic and cationic surfactants at appropriate ratios. The emulsion droplets form water-insoluble filamentous zwitterionic particles upon cooling.

Suitable waxes include but are not limited to the hydrocarbon waxes such as paraffin wax and microcrystallized waxes, waxes derived from natural materials such as beeswax, carnuba wax, triglycerides and other animal and vegetable waxes. The wax may also contain various plasticizers that are used to manipulate their rheological properties and melting point. When cationic carrier particles are desired, a cationic surfactant alone is employed, rather than a mixture of cationic and anionic surfactants. The wax emulsion method of forming filamentous carrier particles is preferred due to ease of manufacture. Typically, the ratio of anionic surfactants to cationic surfactants is in the range of from 9:1 to 0.01:1, preferably in the range of from 2:1 to 0.5:1. The ratio of total surfactant to wax is from about 1:100 to about 1:30. Suitable anionic surfactants are water-soluble alkali metal salts of organic sulfates and sulfonates having alkyl radicals containing from about 8 to about 22 carbon atoms, the term alkyl being used to include the alkyl portion of higher acyl radicals. Examples of suitable synthetic anionic detergent compounds are sodium and potassium alkyl sulfates, especially those obtained by sulphating higher ($C_8$–$C_8$) alcohols produced for examples from tallow or coconut oil, sodium and potassium alkyl ($C_9$–$C_{20}$) benzene sulfonates, particularly sodium linear secondary alkyl ($C_{10}$–$C_{15}$) benzene sulfonates; sodium alkyl glyceryl ether sulfates, especially those ethers of the higher alcohols derived from tallow or coconut oil and synthetic alcohols derived from petroleum; sodium coconut oil fatty monoglyceride sulfates and sulpphonates; sodium and potassium salts of sulphuric acid esters of higher ($C_8$–$C_{18}$) fatty alcohol-alkylene oxide, particularly ethylene oxide, reaction products; the reaction products of fatty acids such as coconut fatty acids esterified with isethionic acid and neutralized with sodium hydroxide; sodium and potassium salts of fatty acid amides of methyl taurine; alkane monosulfonates such as those derived by reacting alpha-olefins ($C_8$–$C_{20}$) with sodium bisulphite and those derived from reacting paraffins with $SO_2$ and $Cl_2$ and then hydrolyzing with a base to produce a random sulfonate; and olefin sulfonates, which term is used to describe the material made by reacting olefins, particularly $C_{10}$–$C_{20}$ alpha-olefins, with $SO_3$ and then neutralizing and hydrolyzing the reaction product. Further examples are described in "Surface Active Agents and Detergents" (Vol. I and II) by Schwartz, Perry and Berch. Any suitable anionic may be used and the examples are not intended to be limiting in any way. Suitable cationic surfactants include but are not limited to quaternary ammonium compounds (such as alkyldimethylammonium halogenides), alkyl and ethoxylated alkyl amines (primary, secondary and tertiary), alkyl pyridinium salts and amidines.

Another suitable way to obtain carrier particles for use in the present invention is to select solid materials with surface reactive groups such as hydroxide, carbonate, sulfate, phosphate, oxide, silicate, (e.g., silica or zeolite), calcium carbonate, titanium dioxide and clays and hydrotalcites, and to react (or engraft) these materials with one or more polymers which contain difunctional organocarbyl groups: one of the groups serves to attach the polymer to the solid material's surface and the second group serves as a functional group on the filament. The second group is, for example, a carboxy group to create a negatively charged filament or an amine to create a positively charged filament. Alternatively, the solid material with the reactive surface group (as described above) may be reacted with polyalkyl glycol, and subsequently modified (e.g., with carboxylamine).

Latex particles with engrafted cationic or zwitterionic surfaces constitute another source of water-insoluble carrier particles for use in the present invention. Suitable latex particles may be obtained commercially from Interfacial Dynamics Corp., Portland, Oreg., telephone: (503) 684-8008. These latex particles have short filaments terminated with functional groups and hydrophobic regions.

In a preferred embodiment of the present invention, zwitterionic particles which have a net negative charge, i.e., particles containing more negatively charged filaments than positively charged filaments, are employed in order to maximize deposition and to minimize formation of flocs.

The carrier particles are present in the inventive composition in an amount of from about 0.1% to about 50%, preferably from about 0.1% to about 20%.

The second essential ingredient included in the inventive compositions is an active substance which, according to the present invention, is delivered along with a carrier particle to a target surface. An active may be a solid or a liquid. According to the present invention, the active is entrapped in, distributed throughout, absorbed or adsorbed by the carrier particles. The identity of the active depends on the particular composition and the particular surface targeted.

When the desired target surface is teeth, or an oral epithelial surface the active material is generally selected from the group consisting of an anticaries compound, an antimicrobial compound, an antiplaque compound, a flavorant, and mixtures thereof. Suitable flavorants include but are not limited to wintergreen oil, oregano oil, bay leaf oil, peppermint oil, clove oil, sage oil, sassafras oil, lemon oil, orange oil, anise oil, benzaladehyde, bitter almond oil, camphor, cedar leaf oil, marjoram oil, citronella oil, lavendar oil, mustard oil, pine oil, pine needle oil, rosemary oil, thyme oil, cinnamon leaf oil, and mixtures thereof. Suitable antimicrobial compounds include but are not limited to thymol, menthol, triclosan, 4-hexylresorcinol, phenol, eucalyptol, benzoic acid, benzoyl peroxide, butyl paraben, salicylamides, and mixtures thereof. Suitable anti-caries compounds include but are not limited to pharmaceutically acceptable fluoride compounds and zinc salts. Typical pharmaceutically acceptable fluoride compounds that are suitable for use in the compositions of this invention include sodium flouride, potassium fluoride, lithium fluoride, aluminum fluoride, zinc fluoride, stannous fluoride, sodium monofluorophosphate, acidulated phosphate fluoride, ammonium fluoride, ammonium bifluoride and amine fluoride. Zinc salts that are suitable for use in the compositions of this invention include zinc chloride, zinc sulfate, zinc acetate, zinc lactate, zinc salicylate, zinc thiocyanate and, more generally, any pharmaceutically acceptable zinc salts.

When the desired target surface is mammalian skin, hair, or nails, suitable active materials include but are not limited to skin anti-ageing compounds, skin conditioning compounds, vitamins, perfumes, antimicrobials, UV-absorbing materials, anti-acne agents, anti-cellulite compounds and mixtures thereof.

Suitable anti-ageing and conditioning compounds include but are not limited to retinoids, $\alpha$-hydroxy acids, salts, and esters thereof, fat-soluble vitamins, ascorbyl palmitate, ceramides, pseudoceramides (e.g., pseudoceramides described in U.S. Pat. Nos. 5,198,210; 4,778,823; 4,985,547; 5,175,321, all of which are incorporated by reference herein), phospholipids (e.g., distearoyl lecithin phospholipid), fatty acids, fatty alcohols, cholesterol, plant sterols, and mixtures thereof. Preferred fatty acids or alcohols are those that have straight or branched alkyl chains containing 12–20 carbon atoms. A particularly preferred fatty acid is linoleic acid since linoleic acid assists in the absorption of ultraviolet light and furthermore is a vital component of the natural skin lipids. The term "retinoid" as used herein includes all natural and/or synthetic analogues of vitamin A or retinol-like compounds which possess the biological activity of vitamin A in the skin as well as the geometric isomers and stereoisomers of these compounds such as all-trans retinoid acid.

Suitable vitamins include but are not limited to vitamin A and vitamin A derivatives, vitamin $B_2$, pantothenic acid, vitamin D, vitamin E.

Suitable skin conditioning agents include but are not limited to long chain fatty acids, liquid water-soluble polyols, glycerin, propylene glycol, sorbitol, polyethylene glycol, ethoxylated/propoxylated ethers of methyl glucose (e.g., methyl gluceth-20) and ethoxylated/propoxylated ethers of lanolin alcohol (e.g., Solulan-75).

Suitable UV-absorbing materials include but are not limited to PABA and PARA amino benzoate derivatives, salicylates, cinnamates, anthranilates, dibenzoyl methanes, camphor derivatives and mixtures thereof. Specific examples include but are not limited to: benzophenone-3, benzophenone-8, ethyldihydroxypropyl-PABA, glyceryl PABA, octyldumethyl PABA, Parsol 1789® (i.e., butyl methoxy debenzoyl methane), homosalate, menthyl anthranilate, octocrylene, octylmethoxy cinnamate, TEA salicylate, octyl salicylate, and mixtures thereof.

Suitable anti-cellulite agents include but are not limitted to isobutylmethylxanthine, caffeine, theophylline, yohimbine, and mixtures thereof.

Suitable anti-acne agents include but are not limited to resorcinol, resorcinol acetate, benzoyl peroxide, salicylic acid, azaleic acid, long chain dicarboxylic acids, various natural agents such as those derived from green tree, and mixtures thereof.

When the desired surface is fabric, suitable active agents include but are not limited to perfumes, whitening agents, brightening agents, fabric softeners.

Of course other active ingredients, not listed in the specific lists or categories above, are suitable for inclusion in the inventive compositions as long as they can be incorporated in the carrier particles.

It should be noted that some active materials may perform more than one function. For instance, menthol may perform both an antimicrobial and flavoring function; fat-soluble vitamins are nutrients for skin, and also serve as conditioning and anti-wrinkle actives.

The active ingredient is deposited on the target surface along with the carrier particles and the active is subsequently gradually released. The release of the active is accomplished by sheer (e.g., rubbing of the particles onto the skin), temperature (e.g., melting of the particles at body temperature), diffusion and combination thereof. The inventive compositions are especially useful for depositing anionic actives.

The active material is present in the inventive compositions in an amount effective to deliver the desired benefit. The particular amount of the active material depends on the identity of the active, the desired benefit, and the nature of the composition. In general, the amount of the active is from about 0.01% to about 50%, preferably from about 0.1% to about 20%, most preferably from about 0.05% to about 2%, by weight of the composition.

An optional but highly preferred ingredient to be included in the inventive compositions is a cationic or amphoteric polymer deposition aid. Suitable amphoteric polymer deposition aids include but are not limited to Merquat 280® (a copolymer of dimethyl/diallyl ammonium chloride and acrylic acid available from Calgon). Suitable cationic polymer deposition aids include but are not limited to the polymers described in U.S. Pat. Nos. 3,761,418; 4,673,525; 4,820,447; 5,064,555; and 4,871,536, all of which are incorporated by reference herein.

The preferred cationic deposition aids are Polyquaternium (CTFA name) polymers, e.g. Polyquaternium-1, Polyquaternium-2, Polyquaternium-4, Polyquaternium-5, Polyquaternium-6, (also known as Merquat 100® available from Calgon), Polyquaternium-7 (also known as Merquat 550® available from Calgon), Polyquaternium-8, Polyquaternium-9, Polyquaternium-10 (also known as Polymer JR 400®), Polyquaternium-11, Polyquaternium-12, Polyquaternium-13, Polyquaternium-14, Polyquaternium-15, Polyquaternium-16, Polyquaternium-17, Polyquaternium-18, Polyquaternium-19, Polyquaternium-20, Polyquaternium-24, Polyquaternium-27, Polyquaternium-28, Polyquaternium-29 (also known as Kytamer KC® available from Amerchol), Polyquaternium-30, Polyquaternium-31, Polyquaternium-32, Polyquaternium-33, Polyquaternium-34, Polyquaternium-35, Polyquaternium-36, Polyquaternium-37, Polyquaternium-39.

The most preferred cationic polymer aids in order to attain maximum deposition are Merquat 100®, Merquat 550®, Polymer JR 400®, and Jaguar C13S® (cationic guar gum).

The amount of the polymeric deposition aid in the inventive compositions is in the range of from about 0.001% to about 5%, preferably from about 0.001% to about 2%.

Although the inventive compositions may be used in any household or personal care product, their use in products containing anionic surfactants is particularly advantageous. Consequently in a preferred embodiment of the invention, the inventive compositions further contain an anionic surfactant. The anionic surfactants are usually water-soluble alkali metal salts of organic sulfates and sulfonates having alkyl radicals containing from about 8 to about 22 carbon atoms, the term alkyl being used to include the alkyl portion of higher acyl radicals. Examples of suitable synthetic anionic detergent compounds are sodium and potassium alkyl sulfates, especially those obtained by sulphating higher ($C_8$–$C_8$) alcohols produced for examples from tallow or coconut oil, sodium and potassium alkyl ($C_9$–$C_{20}$) benzene sulfonates, particularly sodium linear secondary alkyl ($C_{10}$–$C_{15}$) benzene sulfonates; sodium alkyl glyceryl ether sulfates, especially those ethers of the higher alcohols derived from tallow or coconut oil and synthetic alcohols derived from petroleum; sodium coconut oil fatty monoglyceride sulfates and sulfonates; sodium and potassium salts of sulphuric acid esters of higher ($C_8$–$C_{18}$) fatty alcohol-alkylene oxide, particularly ethylene oxide, reaction products; the reaction products of fatty acids such as coconut fatty acids esterified with isethionic acid and neutralized with sodium hydroxide; sodium and potassium salts of fatty acid amides of methyl taurine; alkane monosulfonates such as those derived by reacting alpha-olefins ($C_8$–$C_{20}$) with sodium bisulphite and those derived from reacting paraffins with $SO_2$ and $Cl_2$ and then hydrolyzing with a base to produce a random sulfonate; and olefin sulfonates, which term is used to describe the material made by reacting olefins, particularly $C_{10}$–$C_{20}$ alpha-olefins, with $SO_3$ and then neutralizing and hydrolyzing the reaction product. Another preferred surfactant is an acyl isethionate having the formula:

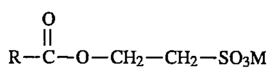

$$R-\overset{O}{\overset{\|}{C}}-O-CH_2-CH_2-SO_3M$$

in which R denotes a linear or branched alkyl group and M denotes an alkali metal or alkaline earth metal or an amine. Further examples are described in "Surface Active Agents and Detergents" (Vol. I and II) by Schwartz, Perry and Berch. Any suitable artionic may be used and the examples are not intended to be limiting in any way.

The amount of an anionic surfactant in the inventive compositions is generally in the range of from about 1% to about 99% by weight of the composition, preferably in the range of from about 1% to about 65%. The particular benefit of the inventive compositions is their ability to deposit anionic actives from compositions containing relatively high concentrations of anionic surfactants.

It has been found as part of the present invention that the pH of the inventive compositions affects the degree of deposition of the zwitterionic particles (and the active entrapped therein). Preferably, in order to improve the deposition from the inventive compositions, the pH of the compositions does not exceed about 10.

The present invention further includes a method of preparing the inventive composition, the method including the steps of incorporating an active substance into a carrier particle, the carrier particle having been prepared by any of the methods described above. In a preferred embodiment of the invention, the resulting particle is mixed with a cationic or an amphoteric deposition aid. When the core of the filamentous carrier particle is a solid material (e.g., zeolite or latex) the active is equilibrated into the solid by diffusion, infusion, absorption or adsorption. When the carrier particle is formed from molten wax emulsion, the active is added to the emulsion so that when the carrier particles with a wax core solidify, the active is entrapped therein. It has been found that when the inventive composition further contains an anionic surfactant, improved (i.e., maximum and uniform) deposition is obtained if the water-insoluble zwitterionic particle is pretreated (i.e., premixed or engrafted with) with the deposition aid, prior to the addition of the anionic surfactant. It was found that in the preparation of inventive composition, mixing for short durations of a few seconds was preferable at least within the range tested. Longer mixing resulted in agglomeration leading to formation of curds, strings and large flocs.

Depending on the nature of the composition, i.e., a skin cleanser, a light duty liquid, a shampoo, a soap bar, etc., the compositions may contain other ingredients suitable for inclusion into such compositions and known to one of ordinary skill in the art.

The following specific examples further illustrate the invention, but the invention is not limited thereto.

EXAMPLES

Experimental Procedure

Materials

Anionic, cationic and zwitterionic polystyrene latex particles were obtained from Interfacial Dynamics Corporation. Sodium dodecyl sulfate (SDS) was purchased from BDH while Merquat® (poly dimethyldiallylammonium chloride) polymers were obtained from Calgon Corp. Polymer JR® and Kytamer® polymers were obtained from Union Carbide Corp. Jaguar C13S® was a product of Rhone Poulenc Corp. Glass slides were biomicroscopic slides purchased from Fisher Scientific Co. All the solutions were prepared using deionized water.

Methods

Deposition

Microscope glass slides were cleaned by dipping in concentrated nitric acid for a minute and washed thoroughly with deionized water to remove all the acid.

Desired microliters of sodium dodecyl sulfate solution were mixed with desired microliters of the polymer and one drop of the latex particles in a cup. The concentrations of polymers and surfactants given in each Example refer to the initial ones. The exact proportions of surfactant:polymer:latex for a given test are indicated in the Tables below. About 3 drops of the resulting mixture were transferred onto the glass slide and particles allowed to sediment for 10 minutes. The slide was washed under a stream of water, allowed to dry and then examined under the optical microscope for the extent of coverage and photographed. Extent of coverage was a relative number based on a visual evaluation of deposition upon comparison of the obtained photographs. All results are accurate within ±5%.

Zeta potential

Zeta potential, a measure of the particle surface potential and hence surface charge, was determined by measuring the velocity of particles in an electric potential gradient. The latex particles were mixed with the solution of polymer and surfactant for a given time at 1% solid concentration and diluted with polymer-surfactant solution or distilled water as indicated to 0.02% solid concentration and the zeta potential was measured immediately thereafter.

EXAMPLE 1

Deposition of Latex Particles in the Absence of the Polymer and the Surfactant

Preliminary deposition studies of latex particles onto bare glass surfaces under natural pH conditions (pH=6.4) were conducted. The results that were obtained are summarized in Table 1.

TABLE 1

| LATEX SURFACE | EXTENT OF COVERAGE (%) |
|---|---|
| Anionic | <5 |
| Cationic | 90 |
| Zwitterionic | 25 |

As expected, best deposition on bare glass slide (negatively charged under the test conditions) was obtained with the cationic latex particles, while practically no deposition was obtained with the anionic sulfate latex. Interestingly, the zwitterionic latex having a net negative zeta potential of −40 mV, identical to that of the anionic latex, coated the negatively charged glass to a significant extent. This higher deposition of zwitterionic particles was unexpected. One possibility is that the zwitterionic particles have patches of anionic or cationic groups and the latter is responsible for the adhesion onto glass surfaces. This can, however, be discounted because the presence of patches would have resulted in instability and flocculation of the zwitterionic particles, and the stable nature of these suspensions prove the contrary to be true.

EXAMPLE 2

Deposition on polymer pretreated surface (two step deposition) Deposition studies were further conducted on glass slides pretreated with the polymeric deposition aid. Deposition of latex particles was evaluated after immersing the glass slide in cationic Merquat 550® (0.1%) and anionic Carbopol® polymer solutions (0.1%) for 3 minutes and rinsing to remove the free polymer. The results that were obtained are given in Table 2.

TABLE 2

| Glass Pretreated With | EXTENT OF COVERAGE (%) Anionic Latex | Cationic Latex | Zwitterionic Latex |
|---|---|---|---|
| Cationic polymer | 70 | <6 | >85 |
| Anionic polymer | 5 | 30 | 50 |

Deposition on the cationic polymer coated surface was, as expected, highest with the artionic latex. Zwitterionic latex particles, however, deposited very well on the cationic polymer coated and quite well on the anionic polymer coated surfaces. This Example demonstrates that both cationic and zwitterionic particles may be used as carrier particles for deposition on negatively charged target surfaces.

EXAMPLE 3

Deposition on bare surfaces from Polymer+Surfactant solutions (one step deposition)

Latex particles were conditioned in premixed surfactant+polymer solutions and deposited on bare glass slides for a given time and then rinsed under a stream of water to remove unattached particles. Deposition of anionic, cationic, and zwitterionic latex particles from 20 mM (0.6%) and 250 mM (7%) sodium dodecyl sulfate solutions were tested with the cationic Merquat 550®, Polymer JR 400®, Polymer JR 30M® (a polymer which is similar to Polymer JR 400®, a substantially higher molecular weight), Celquat SC240® (also known as Polyquaternium-4), and Kytame®, anionic Carbopol® and the amphoteric Merquat 280® polymers. The results that were obtained for deposition from 0.6% sodium dodecyl sulfate solutions and from 7% solutions are summarized in Tables 3A and 3B, respectively.

TABLE 3A

Latex Particles Deposition from 0.6% SDS Solution in the Presence of Polymer
EXTENT OF COVERAGE (%)

| Latex Surface | Polymer (% by weight) | | Cationic (1%) | | | |
|---|---|---|---|---|---|---|
| (SDS:Polymer: Latex Ratio) | Anionic (0.1%) | Amphoteric (1%) | Merquat 550 ® | JR30M ® | JR400 ® | Kytamer ® |
| Anionic (3:1:1) | 0 | 8 | 20 | | 2 | |
| Cationic (3:1:1) | <5 | 5 | 20 | | 5 | |
| Zwitterionic (3:1:1) | 0 | 15 | 35 | | 4 | |
| Anionic (1:1:1) | 0 | 10 | 20 | | 6 | |
| Cationic (1:1:1) | 20 | 8 | 10 | | 10 | |
| Zwitterionic (1:1:1) | 0 | 8 | 25 | | 28 | |
| Anionic (2:1:1) | | | | | 10 | 10 |
| Cationic (2:1:1) | | | | | 15 | 10 |
| Zwitterionic (2:1:1) | | | | | 10 | 10 |

TABLE 3B

Latex Particles Deposition from 7% SDS Solution in the Presence of Polymer
EXTENT OF COVERAGE (%)

| Latex | Polymer (% by weight) | | Cationic | | | | | | |
|---|---|---|---|---|---|---|---|---|---|
| Surface (SDS:Polymer: Latex Ratio) | Anionic (0.1%) | Amphoteric (0.08%) | Merquat 550 ® (0.08%) | JR30M ® (0.08%) | JR400 ® (0.08%) | Jaguar C13S ® (1%) | Celquat SC240 ® (1%) | Merquat 100 ® (1%) | Kytamer ® (0.08%) |
| Anionic (3:1:1) | 0 | 5 | 3 | 3 | | | | | 5 |
| Cationic | 0 | 3 | 0 | 3 | | | | | 5 |
| Zwitterionic (3:1:1) | 1 | 15 | 25 | 25 | | | | | 25 |
| Anionic (1:1:1) | | | | | 3 | | | 20 | |
| Cationic | | | | | 5 | | | 5 | |
| Zwitterionic (1:1:1) | | | | | 30 | | | 25 | |
| Anionic (1:2:1) | | | | | | 25 | 0 | 5 | |
| Cationic 1:2:1) | | | | | | 10 | 0 | 2 | |
| Zwitterionic (1:2:1) | | | | | | 25 | 3 | 5 | |

The results in Tables 3A and 3B indicate that practically no deposition occurred from the anionic Carbopol® solutions; some deposition took place from the cationic and amphoteric polymer solutions. From 0.6% SDS solutions good deposition was obtained in the presence of the cationic Merquat 550®, Kytame®, JR400® and JR30M® solutions. From the 7% SDS solution (SDS:Polymer:Zwitterionic=3:1:1) deposition was obtained in the order shown below:

Merquat 550®≈JR30M®≈Kytamer®>Merquat 280®>Carbopol®

The results indicate better deposition of the zwitterionic latex particles than the anionic or the cationic latexes under most conditions especially under higher (7%) surfactant (SDS) concentrations. For example, deposition of the zwitterionic latex particles obtained from 0.6% sulfate solution (Table 3A) with Merquat 550® and Polymer JR 400M® was higher in comparison to depositions of the other latex particles. Even more importantly, from 7% sulfate solutions (Table 3B) the deposition of the zwitterionic particles obtained with Polymers Merquat 280, Merquat 550®, Polymer JR 30M®, Kytame®, Merquat 100®, and Celquat® was better in comparison to depositions of other latex particles.

EXAMPLE 4

Effect of pH Tests were conducted to evaluate the effect of the pH of the composition on the deposition of zwitterionic latex particles on glass surfaces from 250 mM (7%) SDS solution also containing either an amphoteric (Merquat 280®) or a cationic (Merquat 550®) polymer. Polymer concentration was 0.08% and the ratio SDS:polymer:latex was 3:1:1. The results that were obtained are summarized in Table 5.

TABLE 4

| ESTIMATED % COVERAGE ON GLASS SLIDES | | | |
|---|---|---|---|
| pH | Cationic Polymer | pH | Amphoteric Polymer |
| 2.3 | 8 | 2 | 3 |
| 4.2 | 8 | 4 | 10 |
| 6.0 | 5 | 6.6 | 15 |
| 8.1 | 8 | 9.4 | 5 |
| 10.3 | 0 | 12.3 | 0 |
| 12.0 | 0 | | |

The results in Table 4 indicate significantly lower deposition in the alkaline pH range above 10.

EXAMPLE 5

Order of Addition

The effect of different order(s) of addition of the components in the inventive compositions on the deposition was investigated. Order of mixing tests consisted of mixing first two of the three components (zwitterionic latex, surfactant and polymer) for 10 seconds. This was followed by either mixing with the third component for another ten seconds and then transfer of the mixture onto the slide or transfer onto the slide placed on a horizontal mixer and then mixing with the third component for ten seconds. The results obtained for the order of mixing effects for SDS/Polymer JR400® system are given in Table 6. SDS concentration was 0.075%; Polymer JR400® concentration was 0.075%; the ratio SDS:Polymer:Latex was 4:4:1.

TABLE 5

| Order of Addition | Extent of Coverage (%) |
|---|---|
| (Polymer + Latex) + SDS | >100 (Multilayer) |
| (Polymer + SDS) + latex | <5 |

The results in Table 5 indicate that the order of addition had a dramatic effect on the extent of coverage, with coverage varying anywhere from a few percent for the order (polymer+surfactant)+latex to more than 100% for the order (polymer+latex)+surfactant. It is to be noted that many multilayer patches were obtained in the latter case. Thus, zwitterionic particles pretreated with the polymer deposition aid or with polymer chains appropriately grafted on them might deposit best from concentrated surfactant solutions.

EXAMPLE 6

Effect of Mixing Time

Mixing time effect was studied for only the order (polymer+latex)+surfactant. Polymer JR400® concentration was 0.075%. SDS concentration was 0.07%. The ratio SDS:polymer:latex was 2:2:1. The results that were obtained are summarized in Table 7.

TABLE 6

| Mixing Time | Extent of Coverage (%) |
|---|---|
| 10 seconds | 50 |
| 30 seconds | 30 |
| 3 minutes | 15 |

It was found that mixing for short durations of a few seconds was preferable at least within the range tested. Longer mixing led to agglomeration resulting in formation of curds, strings and large flocs.

EXAMPLE 7

Deposition from Surfactant Solution Without Polymer Aid Deposition of latex particles with various surface charge from 0.6% SDS and SDS solutions onto bare glass surface was measured in the absence of polymeric deposition aid. The SDS:latex ratio was 4:1.

The results that were obtained are summarized in Table 7:

TABLE 7

| | Extent of Coverage (%) | |
|---|---|---|
| LATEX SURFACE | 0.6% SDS | 7% SDS |
| Anionic | 0 | 0 |
| Cationic | 10 | 8 |
| Zwitterionic | 10 | 12 |

EXAMPLE 8

The amount of antimicrobial DP300 deposited from liquid skin cleansing formulation was compared to DP300 deposited from cationic and zwitterionic wax particles. The wax particles were prepared by emulsifying melted wax mixtures in 190 mL of 0.0025 N HCl at 80° C. for 30 min. After cooling to room temperature, stable wax particles of 1–5 μm were obtained. The composition of the zwitterionic wax mixture was as follows:

wax (Baler 1397) 6.5 g dihardened tallow dimethylammonium chloride 0.75 g polyoxyethylene stearylether 1.0 g stearic acid 0.75 g Triclosan DP300 (ex Ciba-Geigy) 1.0 g (10% by weight of wax particle)

The ratio of cationic surfactant and anionic surfactant can be adjusted to obtain wax particles with various charges.

For cationic wax particles, 1.5 g of dihardened tallow dimethylammonium chloride and no stearic acid was used.

The pH of the wax particle solutions was adjusted to 5.5 before addition to the liquid cleansing formulation. The liquid cleanser and the wax particles were mixed in a 1:1 ratio. The liquid cleansing formulation contained 0.1% of Polymer JR 400® and sodium laureth sulfate, sodium cocoyl isethionate, 12.75% of anionic surfactant (6% sodium laurethsulfate and 6.75% cocoylisethionate). 50 μl of a tested formulation was rubbed on human stratum corneum(1 $cm^2$) for 30 sec. and rinsed with water. The amount of DP300 deposited on stratum corneum was determined by HPLC.

The results that were obtained are as follows:

deposition of DP300 without wax particles: 0.8 $\mu g/cm^2$ deposition from cationic wax particles: 2.5 $\mu g/cm^2$ deposition zwitterionic wax particles: 1.5 $\mu g/cm^2$ This example demonstrates the criticality of the inclusion of carrier particles into inventive compositions: a substantial increase in deposition of the active was obtained when the active was incorporated into cationic or zwitterionic carrier particles.

EXAMPLE 9

A suitable liquid soap cleansing formulation within the scope of the invention is as follows:

| INGREDIENT | % BY WEIGHT |
|---|---|
| Sodium Laureth Sulfate | 6.8 |
| Sodium Lauryl Sulfate | 5.0 |
| Lauramide DEA | 2.2 |
| Sodium Sulfate | 2.6 |
| Cocamidopropyl Betaine | 1.8 |
| Sodium Chloride | 0.6 |
| Styrene/Acrylate Copolymer | 0.8 |
| Triclosan containing Wax Particles* | 0.5 |
| Water | to 100% |

*wax particles with Zwitterionic surface described in Example 8.

EXAMPLE 10

Another suitable liquid cleansing formulation within the scope of the invention is as follows:

| INGREDIENT | % BY WEIGHT |
|---|---|
| Sodium Laurel Sulfate | 4.5 |
| Sodium Chloride | 2.0 |
| Quaternium-15 | 1.7 |
| Potassium Cohydrolyzed Collagen | 1.7 |
| Lauryl Polyglucose | 1.6 |
| Cocoamide MEA | 0.4 |
| Wax* Particles Carrying Vitamins** | 0.5 |
| Water | to 100% |

*wax particles with a cationic surface described in Example 8.
**Vitamin A and/or Vitamin E (40% by weight of the wax particles)

EXAMPLE 11

Another suitable liquid soap cleansing formulation is as follows:

| INGREDIENT | % BY WEIGHT |
|---|---|
| Acyl Isethionate | 1–15% |
| Anionic other than Acyl Isethionates (SLES)* | 1–15% |
| Amphoteric Surfactant** | 5–15% |
| Wax particles containing perfume*** | 1–5% |
| Sequestrant (EDTA or EHDP) | 0.01–0.1% |
| Cationic Polymer (Jaguar C13-S ®) | 0.05–3.0% |
| Standard additives (e.g., dyes, perfumes) | 0–10% |
| Water | balance |

*Sodium lauryl ether sulfate
**Cocamidopropyl betaine
***Wax particles with zwitterionic surface prepared in Example 8.

EXAMPLE 12

The following Example illustrates a standard toothpaste composition according to the present invention:

| INGREDIENT | % WEIGHT |
|---|---|
| Alumina trihydrate | 50.00 |
| Sorbitol syrup (70% solution) | 27.00 |
| Sodium lauryl sulfate | 1.50 |
| Sandoperol PLA | 1.50 |
| Sodium carboxymethyl cellulose | 0.85 |
| Sodium monofluorophosphate | 0.76 |
| Sodium saccharin | 0.20 |
| Titanium dioxide | 0.50 |
| Porous Alumina Particles Carrying* | 1.00 |
| Flavor | |
| Water (demineralized) | Balance to 100% |

*Flavor concentration is 50% by weight of the particles

EXAMPLE 13

A typical liquid laundry detergent composition within the scope of the invention is formulated as follows:

| INGREDIENT | % BY WEIGHT |
|---|---|
| Sodium Alkyl Benzene Sulfonate | 20–30 |
| Ethoxyl Glycol Alkyl Ethers | 5–15 |
| Borax ® | 5 |
| Wax particles* carrying perfume | 5 |
| Sodium Citrate | 10–15 |
| Water | Up to 100% |

*Wax particles with cationic surface prepared as in Example 8.

EXAMPLE 14

A typical soap bar composition within the scope of the invention is as follows:

| INGREDIENT | % BY WEIGHT |
|---|---|
| Sodium Cocoyl Isethionate (DEFI) | about 50% |
| Free Fatty Acid | about 20% |
| Anhydrous Soap | about 10% |
| Sodium Stearate | about 5% |
| Sodium Isethionate | about 5% |
| Sodium Alkylbenzenesulfonate | about 2% |
| Miscellaneous (water, colorants, etc.) | about 6% |
| Zwitterionic wax particles carrying perfume | about 2% |
| Total | 100% |

*30% perfume by weight of the particle.

It should be understood that the specific forms of the invention herein illustrated and described are intended to be representative only. Changes, including but not limited to those suggested in this specification, may be made in the illustrated embodiments without departing from the clear teaching of the disclosure. Accordingly, reference should be made to the following appended claims in determining the full scope of the invention.

What is claimed is:

1. A composition for depositing active substances onto a target surface, the composition comprising (i) from about 0.1% to about 50% of carrier particles:

with a zwitterionic surface, the surface having a plurality of outwardly protruding filaments containing positively charged organocarbyl groups selected from the group consisting of primary amine, secondary amine, tertiary amine, quaternary ammonium salts, amidines, pyridinium salts and mixtures thereof and a plurality of outwardly protruding filaments containing negatively charged organocarbyl groups selected from the group consisting of sulfate, sulfonate, carboxylate, phosphate groups, and mixtures thereof, wherein the positively charged groups and the negatively charged groups are located on different filaments;

(ii) from about 0.01% to about 50% of an active substance within said particle, wherein the active substance is a cosmetic active, (iii) from about 1% to about 99% by weight of the composition of an anionic surfactant.

2. The composition of claim 1, wherein the zwitterionic particle has a net negative charge.

3. The composition of claim 1 wherein the composition further comprises cationic or an amphoteric polymer deposition aid.

4. The composition of claim 1 wherein the positively and negatively charged organocarbyl groups are located at the terminal unattached end of the filaments.

5. The composition of claim 1 wherein the zwitterionic surface having filaments is formed from an emulsion comprising molten wax, an anionic surfactant and a cationic surfactant.

6. The composition of claim 1 wherein the cationic surface having filaments is formed from an emulsion comprising molten wax and a cationic surfactant.

7. The composition of claim 1 wherein the water-insoluble particle having a zwitterionic surface is a zwitterionic latex particle.

8. The composition of claim 1 wherein the target surface is negatively charged.

9. The composition of claim 1 wherein the pH of the composition is less than about 10.

10. A composition for depositing active substances onto a negatively charged target surface, the composition comprising (i) from about 1% to about 99% by weight of the composition;

(a) particles with a zwitterionic surface, the surface having a plurality of outwardly protruding filaments containing positively charged organocarbyl groups selected from the group consisting of primary amine, secondary amine, tertiary amine, quaternary ammonium salts, amidines, pyridinium salts and mixtures thereof and a plurality of outwardly protruding filaments containing negatively charged organocarbyl groups selected from the group consisting of surfate, sulfonate, carboxylate, phosphate groups, and mixtures thereof wherein the positively charged groups and the negatively charged groups are located on different filaments;

(ii) from about 0.01% to about 50% of an active substance within said particle. wherein the active substance is a cosmetic active;

(iii) a cationic or an amphoteric polymer deposition aid, (iv) from about 1% to about 99% by weight of the composition of an anionic surfactant.

11. The composition of claim 10 wherein the zwitterionic carrier particle has an overall negative charge.

12. The composition of claim 10 wherein the composition is a skin cleansing composition.

13. The composition of claim 10 wherein the composition is a shampoo.

14. A method of depositing an active substance onto a target surface, the method comprising applying to the target surface the composition of claim 1.

15. The method of claim 14, wherein the target surface is mammalian skin, hair, or nails.

16. The method of claim 14 further comprising rinsing the composition off the target surface.

* * * * *